US008766006B2

(12) United States Patent
Conoci et al.

(10) Patent No.: US 8,766,006 B2
(45) Date of Patent: Jul. 1, 2014

(54) USE OF NITROANILINE DERIVATIVES FOR THE PRODUCTION OF NITRIC OXIDE

(71) Applicant: STMicroelectronics S.r.l., Agrate Brianza (IT)

(72) Inventors: Sabrina Conoci, Tremestieri Etneo (IT); Salvatore Petralia, Modica (IT); Salvatore Sortino, Tremestieri Etneo (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 0 days.

(21) Appl. No.: 13/858,558

(22) Filed: Apr. 8, 2013

(65) Prior Publication Data
US 2013/0224083 A1    Aug. 29, 2013

Related U.S. Application Data

(60) Division of application No. 12/360,004, filed on Jan. 26, 2009, now Pat. No. 8,440,849, which is a continuation-in-part of application No. PCT/IT2006/000575, filed on Jul. 26, 2006.

(51) Int. Cl.
C07C 211/52 (2006.01)
C07C 211/48 (2006.01)
C07C 15/00 (2006.01)
C07F 7/00 (2006.01)
C07C 323/29 (2006.01)
B01J 19/08 (2006.01)
A61K 31/136 (2006.01)
A61K 31/137 (2006.01)

(52) U.S. Cl.
USPC ........... 564/305; 556/136; 556/422; 422/186; 514/646

(58) Field of Classification Search
USPC .................. 564/305; 556/136, 422; 422/186; 514/646
See application file for complete search history.

(56) References Cited

U.S. PATENT DOCUMENTS

| 4,139,595 A | 2/1979 | Vaseen |
| 4,272,336 A | 6/1981 | Vayenas et al. |
| 4,427,504 A | 1/1984 | Stucki |
| 4,774,069 A | 9/1988 | Handley |
| 5,396,882 A | 3/1995 | Zapol |
| 5,427,797 A | 6/1995 | Frostell et al. |
| 5,478,549 A | 12/1995 | Koch |
| 5,827,420 A | 10/1998 | Shirazi et al. |
| 5,839,433 A | 11/1998 | Higenbottam |
| 2004/0081580 A1 | 4/2004 | Hole et al. |
| 2004/0147550 A1 | 7/2004 | Dalton et al. |
| 2005/0038110 A1 | 2/2005 | Steiner et al. |
| 2006/0148893 A1 | 7/2006 | Blanc et al. |
| 2006/0229362 A1 | 10/2006 | Dalton et al. |
| 2008/0058383 A1 | 3/2008 | Jernstedt et al. |
| 2009/0214618 A1 | 8/2009 | Schoenfisch et al. |
| 2009/0227571 A1 | 9/2009 | Loren et al. |

OTHER PUBLICATIONS

Sortino et al., Light-Controlled Nitric Oxide Generation from a Novel Self-Assembled Monolayer on a Gold Surface, Angew. Chem. Int. Ed., 41(11)1914-1917 (2002).*
Bordini et al., "Nitric Oxide Photorelease from Ruthenium Salen Complexes in Aqueous and Organic Solutions," Inorganic Chemistry 41(21): 5410-5416, 2002.
Bourassa et al., "Photochemistry of Roussin's Red Salt, Na2[Fe2S2(NO)4], and of Roussin's Black Salt NH4[Fe4S3(NO)7]. In Situ Nitric Oxide Generation to Sensitive γ-Radiation Induced Cell Death," J. Am. Chem. Soc. 119: 2853-2860, 1997.
Damiani et al., "Fluorometric Determination of Nitrite," Talanta 33(8): 649-652, 1986.
Frost et al., "Controlled Photoinitiated Release of Nitric Oxide From Polymer Films Containing S-Nitroso-N-acetyl-DL-penicillamine Derivatized Fumed Silica Filler," J. Am. Chem. Soc. 126: 1348-1349, 2004.
Frostell et al., "Inhaled nitric oxide. A selective pulmonary vasodilator reversing hypoxic pulmonary vasoconstriction," Circulation 83: 2083-2047, 1991.
Ignarro, "Biosynthesis and Metabolism of Endothelium-Derived Nitric Oxide," Annu. Rev. Pharmacol. Toxicol. 30: 535-560, 1990.
Li et al., "Role of Nitric Oxide in Lysis of Tumor Cells by Cytokine-activated Endothelial Cells," Cancer Research 51: 2531-2535, 1991.
Makings et al., "Caged Nitric Oxide—Stable Organic Molecules From Which Nitric Oxide Can Be Photoreleased," The Journal of Biological Chemistry 269(9): 6282-6285, 1994.
Maragos et al., "Nitric Oxide/Nuclephile Complexes Inhibit the in Vitro proliferation of A375 Melanoma Cells via Nitric Oxide Release," Cancer Research 53: 564-568, 1993.
Miranda et al., "Synthesis and Structural Characterization of Several Ruthenium Porphyrin Nitrosyl Complexes," Inorg. Chem. 36: 4838-4848, 1997.
Misko et al., "A Fluorometric Assay for the Measurement of Nitrite in Biological Samples," Analytical Biochemistry 214: 11-16, 1993.

(Continued)

Primary Examiner — Johann R Richter
Assistant Examiner — Mark Luderer
(74) Attorney, Agent, or Firm — Seed IP Law Group PLLC

(57) ABSTRACT

The present invention relates to the use of a nitroaniline derivative of Formula I for the production of nitric oxide and for the preparation of a medicament for the treatment of a disease wherein the administration of nitric oxide is beneficial. The present invention furthermore relates to a method for the production of NO irradiating a nitroaniline derivative of Formula I, a kit comprising a nitroaniline derivative of Formula I and a carrier and to a system comprising a source of radiations and a container associated to a nitroaniline derivative of Formula I. In Formula I, R and $R^I$ are each independently hydrogen or a $C_1$-$C_3$ alkyl group; $R^{II}$ is hydrogen or an alkyl group.

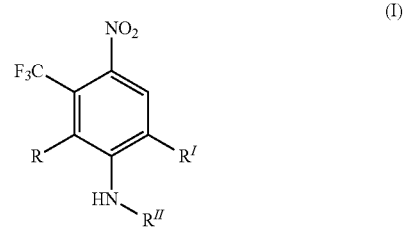

(I)

21 Claims, 9 Drawing Sheets

(56) References Cited

OTHER PUBLICATIONS

Mitchell et al., "Hypoxic Mammalian Cell Radiosensitization by Nitric Oxide," Cancer Research 53: 5845-5848, 1993.

Moncada et al., "Nitric Oxide: Physiology, Pathophysiology, and Pharmacology," Pharmacological Reviews 43(2): 109-142, 1991.

Pepke-Zaba et al., "Inhaled nitric oxide as a cause of selective pulmonary vasodilatation in pulmonary hypertension," Lancet 338: 1173-1174, 1991.

Roberts et al., "Inhaled nitric oxide in persistent pulmonary hypertension of the newborn," Lancet 340: 818-819, 1992.

Sexton et al., "Visible Light Photochemical Release of Nitric Oxide From S-Nitrosoglutathione: Potential Photochemotherapeutic Applications," Photochemistry and Photobiology 59(4): 463-467, 1994.

Sortino et al., "Light-Controlled Nitric Oxide Generation from a Nobel Self-Assembled Monolayer on a Gold Surface," Angew. Chem. Int. Ed. 41(11): 1914-1917, 2002.

Stochel et al., "Light and metal complexes in medicine," Coordination Chemistry Reviews 171: 203-220, 1998.

Suzuki et al., "Photoinduced Nitric Oxide Release from Nitrobenzene Derivatives," J. Am. Chem. Soc. 127: 11720-11726, 2005.

Wang et al., "Nitric Oxide Donors: Chemical Activities and Biological Applications," Chem. Rev. 102: 1091-1134, 2002.

Wink et al., "The multifaceted roles of nitric oxide in cancer," Carcinogenesis 19(5): 711-721, 1998.

Zhelyaskov et al., "Control of NO Concentration in Solutions of Nitrosothiol Compounds by Light," Photochemistry and Photobiology 67(3): 282-288, 1998.

Zhelyaskov et al., "Photolytic Generation of Nitric Oxide through a Porous Glass Partitioning Membrane," Nitric Oxide: Biology and Chemistry 2(6): 454-459, 1998.

* cited by examiner

USE OF NITROANILINE DERIVATIVES FOR THE PRODUCTION OF NITRIC OXIDE

BACKGROUND

1. Technical Field

The present disclosure relates to the use of a nitroaniline derivative for the production of nitric oxide, in particular in the preparation of a medicament for treating diseases wherein the administration of nitric oxide may be beneficial. The present disclosure further relates to a kit comprising a nitroaniline derivative and to a system for the production of nitric oxide.

2. Description of the Related Art

Nitric oxide (NO) has been shown to play a significant role in the regulation of many biochemical pathways in organisms ("Nitric oxide: Physiology, Pathophysiology, and Pharmacology", M. Moncada et al, *Pharmacological Review, vol.* 43(2), pages 109-142, 1991 and "Biosynthesis and Metabolism of Endothelium-derived Nitric Oxide", L. J. Ignarro, *Ann. Rev. Pharmacol. Toxicol., vol.* 30, pages 535-560, 1990). Nitric oxide has been proven to be an important modulator of vascular, cardiovascular, nervous and immune systems as well as other homeostatic mechanisms ("Inhaled Nitric Oxide: A selective pulmonary vasodilator reversing human hypoxic K pulmonary vasoconstriction (HPV)", Z. Blomquist, *Circulation, vol.* 84, No. 4, page 361, 1991 and "Involvement of nitric acid in the reflex relaxation of the stomach to accommodate food or fluid", K. M. Desai et al., *Nature, vol.* 351, No. 6, page 477, 1991). Desai et al demonstrated that adaptive relaxation in isolated stomach of the guinea pig is mediated by a non-adrenergic, non-cholinergic (NANC) neurotransmitter. Furthermore, they showed that this NANC neurotransmitter is undistinguishable from nitric oxide derived from L-arginine. The authors concluded that it is likely that nitric oxide is a final common mediator of smooth muscle relaxation.

Smooth muscles are present, for example, in the walls of the blood vessels, bronchi, gastrointestinal tract, and urogenital tract. Administration of nitric oxide gas to the lung by inhalation could produce localized smooth muscle relaxation without systemic side effects. This characteristic can be used in medicine to treat bronchial constriction and pulmonary hypertension, pneumonia, etc.

To date, conventional treatment of pulmonary and cardiovascular abnormalities has primarily involved the use of bronchodilators drugs.

Bronchodilators, such as beta-agonists and anticholinergic drugs, are used to reduce airway reactivity and to reverse bronchospasm caused by a variety of diseases, such as asthma, exacerbations of chronic pulmonary obstructive disease, allergic and anaphylactic reactions and others.

Beta-agonists induce bronchodilation by stimulating receptors that increase adenyl cyclase concentrations and the production of intracellular cyclic adenosine monophosphate (AMP). They can be delivered by aerosol, orally or parenterally. Administration of these agents causes significant adverse cardiac effects such as tachycardia, heart palpitations, changes in blood pressure and also other side effects including anxiety, tremors, nausea and headaches. Newer beta2-selective agonists have fewer side effects and somewhat slower onset of action.

Anticholinergic drug, administered by aerosol, are effective bronchodilators with relatively few side effects. However, they have a slow onset of action, and 60 to 90 minutes may be required before peak bronchodilation is achieved.

Nitric oxide is unique in that it combines a rapid onset of action occurring within seconds with the absence of systemic effects. Once inhaled, it diffuses through the pulmonary vasculature into the bloodstream, where it is rapidly inactivated by combination with hemoglobin. Therefore, the bronchodilator effects of inhaled nitric oxide are limited to the airway and the vasodilatory effects of inhaled nitric oxide are limited to the pulmonary vasculature.

The usage of inhaled NO gas as a selective therapeutic agent for the treatment of pulmonary and cardiovascular ailments is also reported in "Inhaled nitric oxide as a cause of selective pulmonary vasoldilation in pulmonary hypertension", J. Perke-Zaba et al, *The Lancet*, vol. 338, No. 9, page 1173, 1991. It has recently been established that the administration of 5 to 80 ppm of NO in respiratory gases drastically improves persistent pulmonary hypertension of newborn children within a few minutes. This important medical application of NO gas is discussed in "Inhaled nitric oxide in persistent pulmonary hypertension of the newborn" by J. D. Roberts et al., *The Lancet*, vol. 340, pages 818-819, 1992.

In addition to these effects, NO has also been reported to act as efficient anticancer agent that inhibits key metabolic pathways to block the growth of or to kill cells (C. M. Maragos, J. M. Wang, J. A. Hrabie, J. J. Oppenheim, L. K. Keefer, *Cancer Res.* 1993, vol. 53, page 564; J. B. Mitchell, D. A. Wink, W. DeGraff, J. Gamson, L. K. Keefer, M. C. Krishna, *Cancer Res.* 1993, vol. 53, page 5845; L. Li, R. G. Kilbourn, J. Adams, I. J. Fidler, *Cancer Res.* 1991, vol. 52, page 2531; R. J. Griffin, C. W. Song, Presented at the 43rd Annual Meeting of the Radiation Research Society, San Jose, Calif., April 1995; Abstract P15-204; D. Moncada, D. Lekieffre, B. Arvin, B. Meldrum, Neuroreports 1993, vol. 343, page 530; D A Wink, Y Vodovotz, J Laval, F Laval, M W Dewhirst, and JB Mitchell, *Carcinogenesis vol.* 19, no. 5, page 711-721, 1998).

The failure of NO therapy to achieve widespread usage is primarily attributable to the previous lack of a precision NO gas generator suitable for clinical and biomedical applications.

It is known to produce NO through different methods such as thermal methods, electrochemical methods or photochemical methods.

Molecular systems useful in thermal methods are extensively studied in the literature (Peng George Wang, Ming Xian, Xiaoping Tang, Xuejun Wu, Zhong Wen, Tingwei Cai, and Adam J. Janczuk, *Chem. Rev.* 2002, vol. 102, pages 1091-134; Zhelyaskov, V. R., Godwin, D. W., and Gee, K., *Photochem. Photobiol.,* 1998, vol. 67, pages 282-288). The main disadvantage of these methods is that the NO release is not controllable and can not be achieved on demand.

Therefore, the implementation of these methods in medical device is not suitable and to date it does not exist in any medical device based on such methods.

Electrochemical and electrical methods allow accurate delivery of variable concentrations of NO upon electrical stimuli. They can allow a controllable on demand release of NO.

However, the implementation of these methods in devices for medical applications gives rise to complex systems, often not applicable to clinical or home use and in some cases based on process susceptible to fluctuations in internal and external operating parameters.

In this context, historically NO gas has been commercially manufactured using the well-known Ostwald process in which ammonia is catalytically converted to NO and nitrous oxide at a temperature above 800 DEG C. The Ostwald process is discussed in U.S. Pat. Nos. 4,272,336; 4,774,069 and 5,478,549. The Ostwald process, while suitable for the mass production of NO at high temperatures in an industrial setting, is clearly not applicable to clinical or home use. Other methods of NO gas generation are based on Haber-Bosch synthesis, as described in U.S. Pat. No. 4,427,504, or by taking advantage of paramagnetic properties of nitrous oxide, as described in U.S. Pat. No. 4,139,595.

None of these techniques is suitable for clinical or home use and significant industrial application thereof has not been reported. Yet another method for the generation of NO, which has found limited use in analytical laboratories, relies upon the reaction of 8 molar nitric acid with elemental copper. This method is described by F. A. Cotton in the text "Advanced Inorganic Chemistry", 5th edition, pages 321-323, John Wiley & Sons, New York, 1988.

There have been recent attempts to devise apparatus for accurately delivering variable concentrations of NO.

By way of example, U.S. Pat. No. 5,396,882 describes a proposal for the generation of NO in an electric discharge in air. In the implementation of this proposed technique, electrodes would be separated by an air gap in an arc chamber. The establishment of a high voltage across the air gap would produce a localized plasma for breaking down oxygen and nitrogen molecules and thereby generate a mixture of NO, ozone and other $NO_x$ species. In theory, the concentration of NO could be varied by adjusting the operating current. The gas mixture produced by the process would be purified and mixed with air in order to obtain therapeutically significant concentrations of NO for administration to a patient. The process proposed in U.S. Pat. No. 5,396,882 would, however, inherently be susceptible to fluctuations in internal and external operating parameters, particularly the ambient humidity. Since the therapeutically useful range of NO concentration is relatively small, it is imperative that the concentration of administered NO be precisely controlled. In the process of U.S. Pat. No. 5,396,882, for example, the achievement of such control would dictate that the NO concentration be closely monitored at all times. Since the weight of NO generated by the process of U.S. Pat. No. 5,396,882 will vary with fluctuations in operating parameters, the monitoring of NO concentration would, at best, be extremely difficult and expensive to achieve. Indeed, a chemiluminescence analyzer would have to be incorporated into the apparatus and the size and cost of such an analyzer would adversely affect the cost and portability of the apparatus.

U.S. Pat. No. 5,827,420 describes an electrochemical process based on the production of NO through the coulometric reduction of copper (II) ions ($Cu^{2+}$) in a solution of nitric acid accompanied by purging the reaction chamber with an inert gas such as nitrogen. The method permits precise control over the rate of production of nitric oxide and can be used for free-standing, portable coulometric generator of controllable amounts of high purity nitric oxide. Nevertheless, such an apparatus is a complex system (several reaction cells, cylinder for carrier gas) that needs the presence of several toxic solutions at high concentration (8M nitric acid, 0.1 $CuSO_4$).

Photochemical methods allow the release of NO in a controllable and precise way on demand upon light stimuli. There are a limited number of compounds able to generate NO using light as trigger that are known in the state of the art (Bordini J., Hughes D. L., Da Motta Neto J. D., Jorge da Cunha C., *Inorg. Chem.*, 2002, vol. 41(21), pages 5410-5416; G. Stochel, A. Wanat, E. Kulis, Z. Stasicka, *Coord. Chem. Rev.*, 1998, vol. 171, pages 203-220; S. Wecksler, A. Mikhailovsky, P. C. Ford, *J. Am. Chem. Soc.*, 2004, vol. 126, pages 13566-13567; J. Baurassa, W. DeGraff, S. Kudo, D. A. Wink, J. B. Mitchell, P. C. Ford, *J. Am. Chem. Soc.* 1997, vol. 119, page 2853; K. M. Miranda, X. Bu, I. Lorkovic, P. Ford, *Inorg. Chem.* 1997, vol. 36, page 4838; V. R. Zhelyaskov, K. R. Gee, D. W. Godwin, *Photochem. Photobiol.* 1998, vol. 67, page 282; L. R. Makings, R. Y. Tsien, *J. Biol. Chem.* 1994, vol. 269, page 6282; D. J. Sexton, A. Muruganandam, D. J. McKenney, B. Mutus, *Photochem. Photobiol.*, 1994, vol. 59, page 463; M. C. Frost, M. E. Meyerhoff, *J. Am. Chem. Soc.* 2004, vol. 126, pages 1348-1349; T. Suzuki, O, Nagae, Y. Kato, H. Nakagawa, K. Fukuhara, N. Miyata, J. Am. Chem. Soc., 2005, vol. 127, pages 11720-11726).

Among these, the majority is activated by light in the ultra-violet (UV)-range that, is not only biologically dangerous, but also requires complex instrumentation and is not suitable to be integrated in miniaturized and portable devices.

Only limited examples of NO donors activated by visible light are known (Valentin R. Zhelyaskov and Dwayne W. Godwin, "NITRIC OXIDE: Biology and Chemistry", Vol. 2, No. 6, pages 454-459 (1998); Bordini J., Hughes D. L., Da Motta Neto J. D., Jorge da Cunha C., *Inorg. Chem.*, 2002, vol. 41(21), pages 5410-5416; J. Baurassa, W. DeGraff, S. Kudo, D. A. Wink, J. B. Mitchell, P. C. Ford, *J. Am. Chem. Soc.* 1997, vol. 119, page 2853). However, their chemical structures are not adequate for easy chemical derivatization in order to allow their assembly onto films and nanoparticles. Moreover, one potential disadvantage of these compounds is related to the toxic effect of their photoproducts. This requires complex apparatus in order to avoid diffusion of the toxic caging moiety.

Finally, it is known to use a compound of Formula

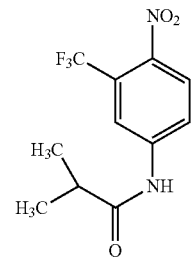

commonly known as Flutamide, for the production of NO via UV-visible light irradiation (S. Sortino, S. Petralia, G. Compagnini, S. Conoci and G. Condorelli, Light-Controlled Nitric Oxide Generation from a Novel Self-Assembled Monolayer on Gold Surface, *Angew. Chem. Int. Ed.* 2002-41/11, 1914-1917).

Disadvantageously, this compound shows some limitations related to the fact that only a very small portion of its absorption falls in the visible region of the electromagnetic spectrum and therefore long irradiation times and expensive devices are needed to obtain acceptable yields of NO.

BRIEF SUMMARY

Certain embodiments provide the use of new compounds able to generate NO and a method for the production of NO that are free from the above described drawbacks and in particular are free from toxic effects and allow for an easy derivatization.

One embodiment provides a method comprising:

converting nitroaniline derivatives of Formula (I) to nitric oxide:

$$\text{(I)}$$
[Structure: benzene ring with NO2 (para), F3C (meta), R, R', and HN-R'' (ortho/amine)]

wherein, R and R' are each independently hydrogen or a C₁-C₃ alkyl group; and R'' is hydrogen or a substituted or unsubstituted alkyl group, the converting including irradiating the nitroaniline derivatives of Formula (I) with radiation having a wavelength between 300 nm to 500 nm.

Another embodiment provides a method of administering nitric oxide gas to a subject in need thereof, comprising:

generating nitric oxide gas by irradiating a nitroaniline derivative of Formula (I) with radiation having a wavelength of about 300 nm to 500 nm:

$$\text{(I)}$$

wherein, R and R' are each independently hydrogen or a C₁-C₃ alkyl group; and R'' is hydrogen or a substituted or unsubstituted alkyl group; and introducing the nitric oxide gas into an airway of the subject.

A further embodiment provides compounds well-suited to be employed in miniaturized, low cost and portable medical devices.

One embodiment provides a kit comprising:

a nitroaniline derivative of Formula (I):

$$\text{(I)}$$

wherein, R and R' are each independently hydrogen or a C₁-C₃ alkyl group; R'' is hydrogen or a substituted or unsubstituted alkyl group; and a carrier.

Another embodiment provides a system comprising:

a source of radiation having a wavelength of between 300 and 500 nm;

a support or container associated to a nitroaniline derivative of Formula (I):

$$\text{(I)}$$

wherein R and R' are each independently hydrogen or a C₁-C₃ alkyl group; R'' is hydrogen or a substituted or unsubstituted alkyl group; and a carrier.

A further embodiment provides a method comprising:

administering nitric oxide gas to a subject in need thereof, the administering including: generating nitric oxide gas by irradiating a nitroaniline derivative of Formula (I) with radiation having a wavelength of about 300 nm to 500 nm:

$$\text{(I)}$$

wherein R and R' are each independently hydrogen or a C₁-C₃ alkyl group; and R'' is hydrogen or a substituted or unsubstituted alkyl group; and introducing the nitric oxide gas into an airway of the subject.

DETAILED DESCRIPTION

Figure 1:
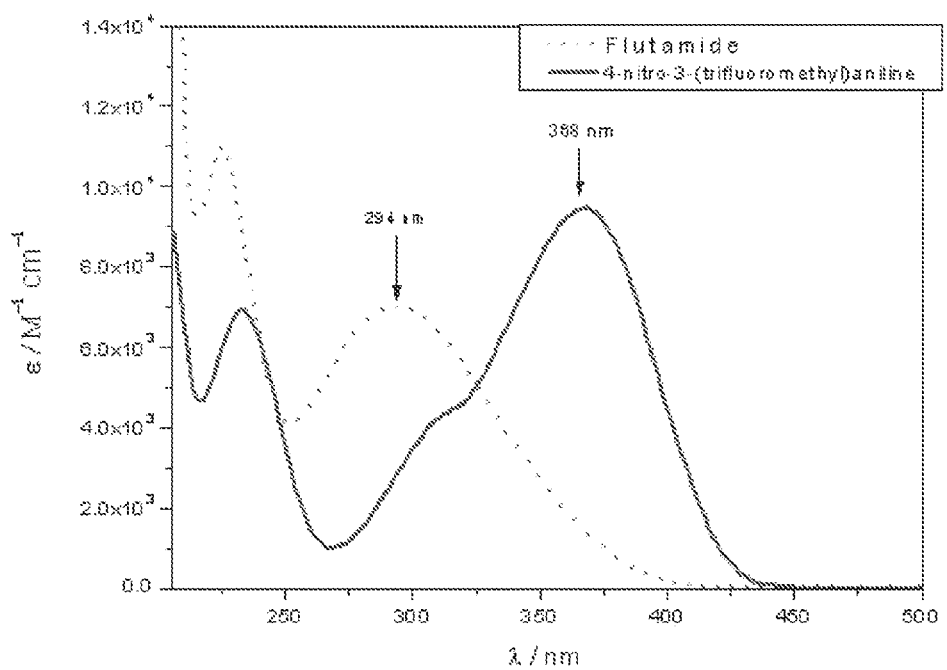
FIG. 1 shows the absorption spectrum of the nitroaniline derivatives of Formula (I).

Certain embodiments describe a nitroaniline derivative of Formula (I), a method for the production of nitric oxide using the same, a kit and a system including the same, and a method of administering nitric oxide.

In particular, one embodiment provides a method of converting a nitroaniline derivative of Formula (I) to nitric oxide, the converting comprising: irradiating the nitroaniline derivatives of Formula (I) with radiation having a wavelength between 300 nm to 500 nm:

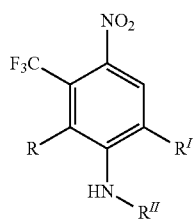

(I)

wherein:

R and $R^I$ are each independently hydrogen or a $C_1$-$C_3$ alkyl group;

$R^{II}$ is hydrogen or a substituted or unsubstituted alkyl group.

In certain embodiments, $R^{II}$ is Ak-Y, wherein Ak is a branched or unbranched $C_2$-$C_{18}$ alkyl group optionally substituted with —OH or $NH_2$, and Y is a tail-group selected from the group consisting of hydrogen, halogen, —SH, —S—$SR^{III}$, —Si$(OR^{IV}_3)_3$, —Si—$X_3$, and —CH=$CR^V R^{VI}$, wherein $R^{III}$ is selected from the group consisting of alkyl group, aryl group, aralkyl group, alkenyl group, alkynyl group and heterocyclic group; $R^{IV}$ is an alkyl group; $R^V$ and $R^{VI}$ are independently hydrogen or alkyl group; X is halogen, more preferably chlorine or bromine. Preferably, $R^{III}$ is an alkyl group, more preferably a $C_1$-$C_{30}$ alkyl group.

As used herein, "alkyl" or "Ak" refers to a straight (i.e., unbranched) or branched hydrocarbon chain radical comprising carbon and hydrogen atoms, containing no unsaturation, having from one to thirty carbon atoms (i.e., $C_1$-$C_{30}$ alkyl). In certain embodiments, an alkyl may comprise two to eighteen carbon atoms (i.e., $C_2$-$C_{18}$ alkyl). In other embodiments, an alkyl may comprise one to three carbon atoms (i.e., $C_1$-$C_3$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

"Alkenyl" refers to a straight or branched hydrocarbon chain radical group comprising carbon and hydrogen atoms, containing at least one double bond, and having from two to twelve carbon atoms. In certain embodiments, an alkenyl may comprise two to eight carbon atoms. In other embodiments, an alkenyl may comprise two to four carbon atoms. The alkenyl is to the rest of the molecule by a single bond, for example, ethenyl (i.e., vinyl), prop-1-enyl (i.e., allyl), but-1-enyl, pent-1-enyl, penta-1,4-dienyl, and the like.

"Alkynyl" refers to a straight or branched hydrocarbon chain radical group comprising carbon and hydrogen atoms, containing at least one triple bond, having from two to twelve carbon atoms. In certain embodiments, an alkynyl may comprise two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2)π-electron system in accordance with the Hückel theory. Aryl groups include, but are not limited to, groups such as phenyl, fluorenyl, and naphthyl.

"Aralkyl" refers to an alkyl (as defined herein) substituted with an aryl group, for example, benzyl, diphenylmethyl and the like.

"Halogen" refers to bromo, chloro, fluoro or iodo.

"Heterocyclic group" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical may be a monocyclic, bicyclic, tricyclic or tetracyclic ring system, which may include fused or bridged ring systems. The heteroatoms in the heterocyclyl radical may be optionally oxidized. One or more nitrogen atoms, if present, may be optionally quaternized. The heterocyclyl radical may be fully saturated (e.g., tetrahydrofuranyl), partially unsaturated or fully unsaturated (e.g., pyridinyl). The heterocyclyl may be attached to the rest of the molecule through any atom of the ring(s).

"Optionally substituted" means that, any of the above-described radical group may or may not be substituted with one or more substituents. Unless specified otherwise, the description of any of the above radical groups (e.g., alkyl, alkenyl, alkynyl, aryl, aralkyl, heterocyclic group) includes both unsubstituted radicals and radicals substituted with one or more of the following groups: halogen, cyano, nitro, oxo, thioxo, trimethylsilanyl, —$OR^a$, —Si$(OR^a)_3$, —$SR^a$, —OC(O)—$R^a$, —N$(R^a)_2$, —C(O)$R^a$, —C(O)O$R^a$, —C(O)N$(R^a)_2$, —N$(R^a)$C(O)O$R^a$, —N$(R^a)$C(O)$R^a$, —N$(R^a)$S(O)$_t R^a$ (where t is 1 or 2), —S(O)$_t$O$R^a$ (where t is 1 or 2) and —S(O)$_t$N$(R^a)_2$ (where t is 1 or 2) where each $R^a$ is independently hydrogen, alkyl, aryl, aralkyl, heterocyclic group.

According to one embodiment, the nitroaniline derivative of Formula (I) is 4-nitro-3-(trifluoromethyl)aniline.

The method allows to produce in very precise and controlled way nitric oxide.

Advantageously, nitroaniline derivatives of Formula (I) present an excellent solubility in water solution and a very high chemical stability over a wide range of pH (tested via HPLC-ESI-MS). Moreover, they allow an easy derivatization. All these properties are essential prerequisites for biological applications in medical devices, in particular for the employment in miniaturized low cost and portable devices.

Further, the photochemical nitroaniline derivatives of Formula (I) are able to produce NO by visible light irradiation, in particular when irradiated with radiations having a wavelength of between 300 and 500 nm, preferably between 400 and 450 nm.

Advantageously, nitroaniline derivatives of Formula (I) present a very good overlap of their absorption spectrum with the visible region of electromagnetic spectrum (see FIG. 1) in contrast to the know compounds and, in particular, the aforementioned Flutamide.

The shift of the absorbance curve of nitroaniline derivatives of Formula (I) compared to the absorbance curve of Flutamide is caused by the substitution of the amide group of Flutamide with an amine group.

This substitution was proved to cause a great variation of the molar extinction coefficient of the chromophore and the shift of the absorbance towards longer wavelengths, thus allowing the molecule excitation with light having lower frequency.

Advantageously, the inventors found that the substitution of the amide group of Flutamide with an amine group does not affect the ability of the photochemical group of nitroaniline derivatives of Formula (I) to produce NO when irradiated with appropriated wavelengths.

In particular, they have found that nitroaniline derivatives of Formula (I), when irradiated with radiations having a wavelength of between 300 and 500 nm, undergo a radical reaction to generate NO, as shown in the scheme below.

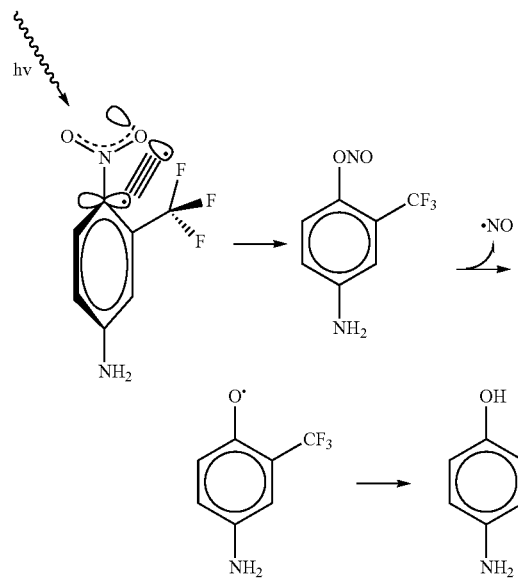

The mechanism of NO photo-generation of nitroaniline derivatives of Formula (I) is based on a nitro-to-nitrite photo-rearrangement followed by the formation of a phenoxy radical as the main transient intermediate and a phenol derivative as a stable end product in agreement with literature.

At the end of the reaction, 4-hydroxy-3-(trifluoromethyl) aniline derivatives are produced. These photoproducts are phenol-derivatives that, according to similar compounds, are potential antioxidants. This overcomes the toxicity problems of photoproducts of other NO photo-generators (Bordini J., Hughes D. L., Da Motta Neto J. D., Jorge da Cunha C., *Inorg. Chem.*, 2002, vol. 41(21), pages 5410-5416; G. Stochel, A. Wanat, E. Kulis, Z. Stasicka, *Coord. Chem. Rev.*, 1998, vol. 171, pages 203-220; K. M. Miranda, X. Bu, I. Lorkovic, P. Ford, *Inorg. Chem.* 1997, vol. 36, page 4838).

Figure 2:
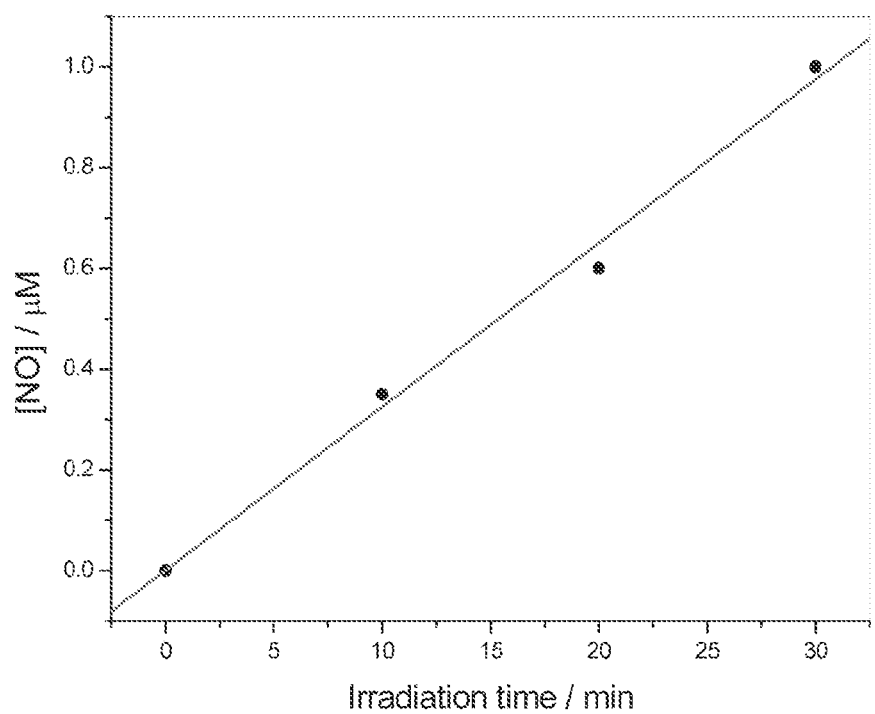
FIG. 2 shows the concentration of NO released from an aqueous solution of NOME $10^{-4}$ M detected with a fluorimetric as a function of time.
Figure 3:
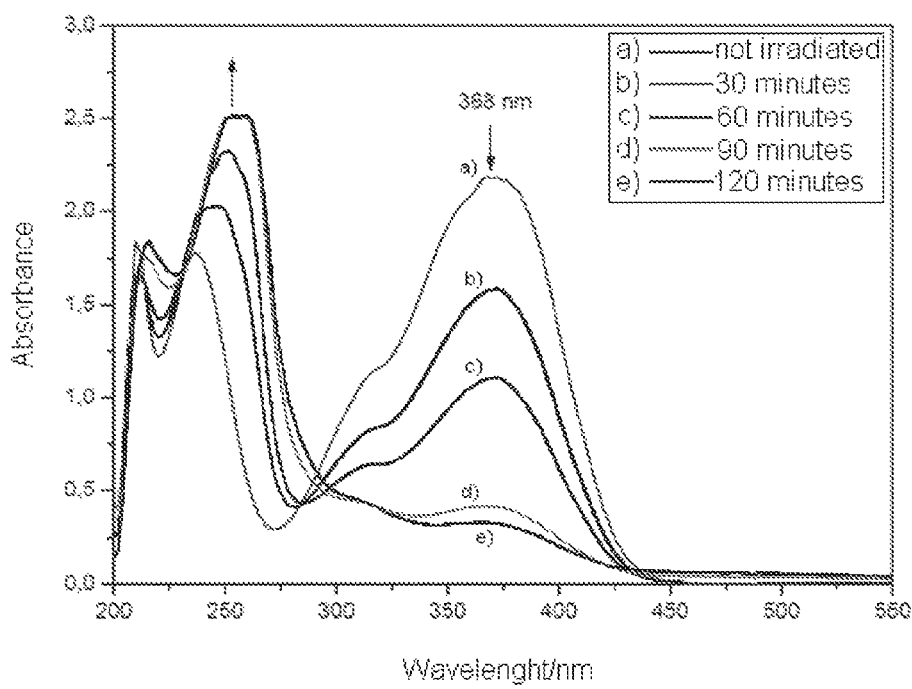
FIG. 3 shows the absorption spectra of 4-nitro-3-(trifluoromethyl)aniline in methanol measured every 30 minutes over a two-hour period.
Figure 4:
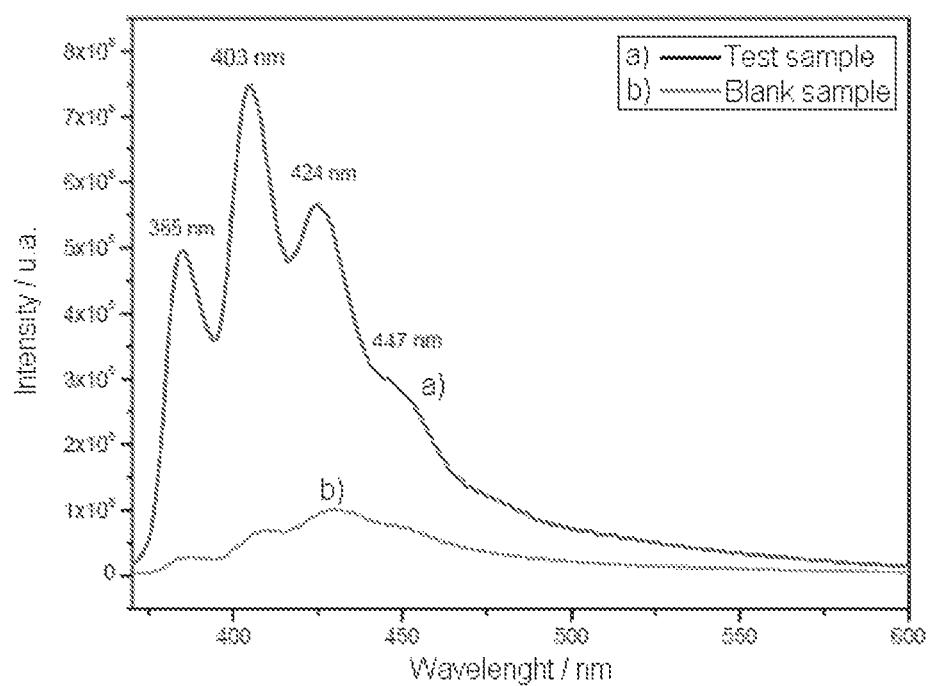
FIG. 4 shows the fluorescent spectrum that indicates the presence of nitrites and therefore the formation of NO following irradiation of a 4-nitro-3-(trifluoromethyl)aniline solution.
Figure 5:
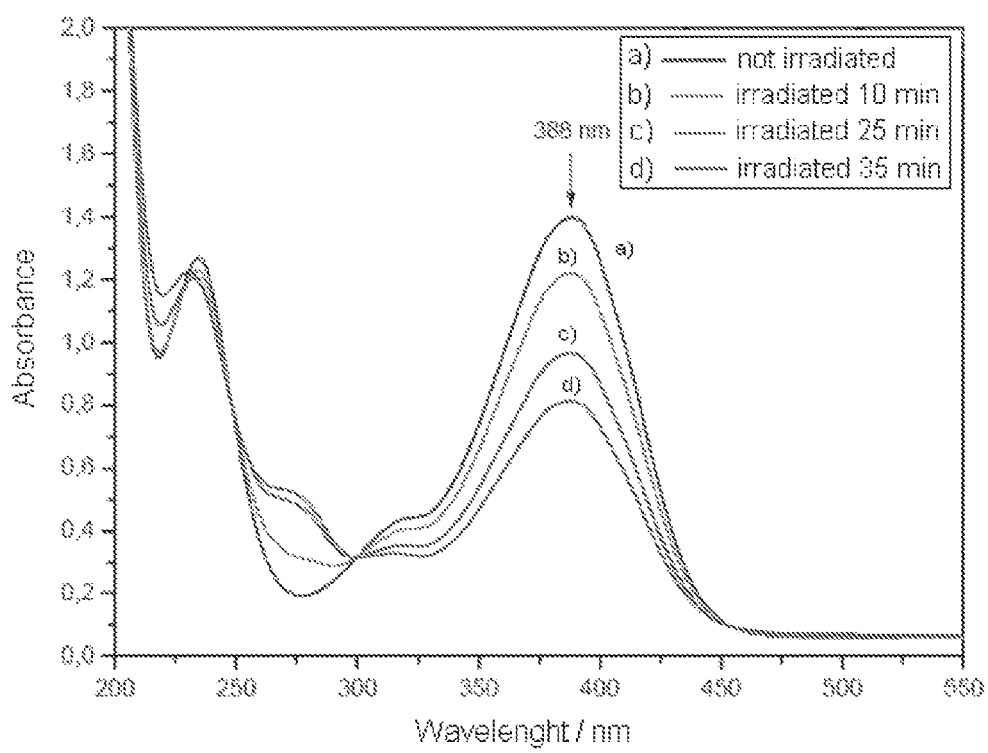
FIG. 5 shows absorbance, measured at 30 minute intervals, of a 1043-(trifluoromethyl)-4-nitrophenylamino)decan-1-thiol in a CH₃OH:H₂O (10%) solution.
Figure 6:
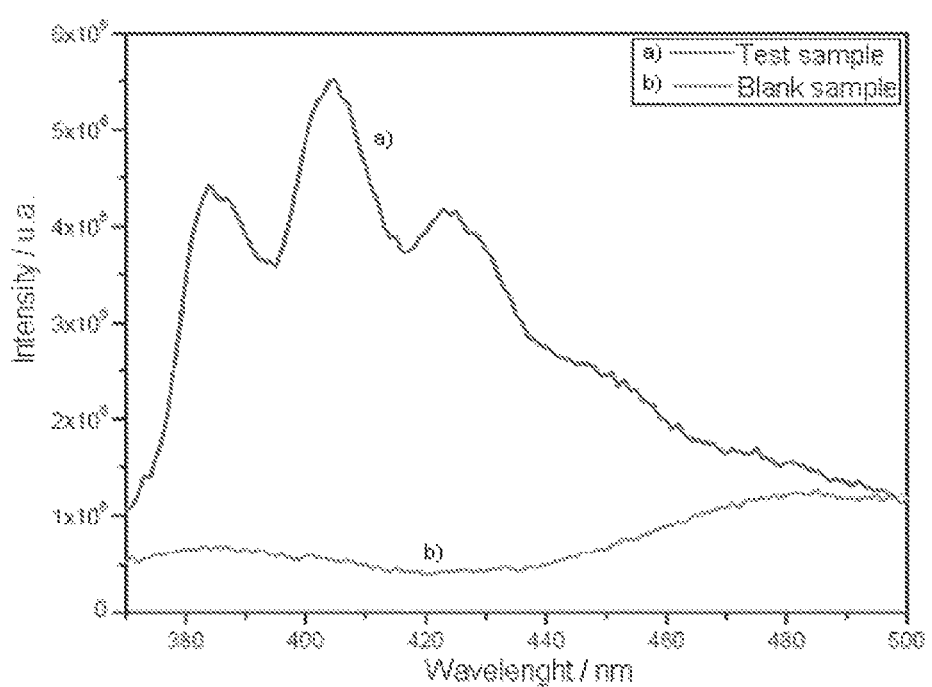
FIG. 6 shows the fluorescent spectrum that indicates the presence of nitrites and therefore the formation of NO following irradiation of a 10-(3-(trifluoromethyl)-4-nitrophenylamino)decan-1-thiol solution.

In particular, the ability of nitroaniline derivatives of Formula (I) to generate NO upon 400 nm light irradiation is reported in FIG. 2.

FIG. 2 represents the concentration of NO released, detected with a fluorimetric assay (T. P. Misko, R. J. Schilling, D. Salvemini, W. M. Moore, M. G. Currie, *Anal. Chem.*, 1993, 214, 11.), as a function of time from an aqueous solution of NOME $10^{-4}$M.

Because their absorption spectra are in the visible range of the light, nitroaniline derivatives of Formula (I) can be integrated in a very small, portable device.

Moreover, the use of visible light instead of UV, permits direct application in biological sample without any risk of phototoxicity.

The nitroaniline derivatives of Formula (I) can be in a liquid or in a solid form and can be associated to a carrier. The carrier preferably has a minor molar absorptivity in the wavelength of between 300 and 500 nm, i.e., less than 15%, preferably 10%, more preferably less than 5% of that of the nitroaniline derivative associated therewith.

The carrier can be a liquid solution, for example an aqueous solution, or a solid substrate, for example in the form of nanoparticles or bi-dimensional surfaces, selected from the group consisting of a metal, an inorganic oxide, silicon and a plastic polymeric material.

The preferred metals are selected from the group consisting of gold, platinum and silver, and the preferred inorganic oxides are silicon oxide ($SiO_x$) or indium tin oxide (ITO).

In one embodiment, the nitroaniline derivatives of Formula (I) are chemically bound to the solid substrate, provided that the formation of an amide bond between the amine group of the nitroaniline derivative of Formula (I) and the solid substrate is avoided. In fact, the presence of a carboxy group adjacent to the amine group of the nitroaniline derivatives of Formula (I) has proved to cause the shift of the absorbance of the nitroaniline derivatives of Formula (I) to wavelengths in the UV spectrum.

Preferably, when the tail-group of nitroaniline derivatives of Formula (I) is —SH or —S—$SR^{II}$, a metallic substrate can be used as a carrier; when the tail-group is —Si($OR^{III}_3$)$_3$ or —Si—$X_3$, inorganic oxides can be used as a solid substrate and when the tail-group is —CH=$CR^{IV}R^V$, a silicon substrate can be used.

The solid substrate can be, for example, in the form of nanoparticles bearing the nitroaniline derivatives of Formula (I) on their surface, in the form of bi-dimensional elements on which a layer of a nitroaniline derivative of Formula (I) is deposited or in the form of a porous solid, soaked with a nitroaniline derivative of Formula (I).

The present disclosure also relates to the use of a nitroaniline derivative of Formula (I) as described above, for the preparation and administration of NO for the treatment of a disease wherein the administration of nitric oxide is beneficial.

Preferably the disease can be selected in the group consisting of respiratory diseases, cancers, and vascular diseases.

As described above, nitroaniline derivatives of Formula (I) can be associated to a carrier, preferably having minor molar absorptivity in the wavelength range of between 300 and 500 nm.

For example, it is possible to use as a carrier an aqueous solution of metal nanoparticles covalently coated with nitroaniline derivatives of Formula (I) that can be firstly delivered in the human body and then externally (to the human body) irradiated. This is particularly suitable for in vivo application.

One embodiment is a method for the production of nitric oxide comprising the step of irradiating a nitroaniline derivative of Formula (I), as described above, with radiations having a wavelength comprised between 300 and 500 nm, preferably between 400 and 450. The nitroaniline of Formula (I) can be associated to one of the above-mentioned carriers, transparent to visible light.

One embodiment is a kit comprising a nitroaniline derivative of Formula (I) and a carrier as described above.

One embodiment is a system comprising a source of radiations having a wavelength of between 300 and 500 nm and a support or container associated to the above-described nitroaniline derivative of Formula (I).

Advantageously, while molecular systems that use UV light need very large and expensive lamps, also having a short lifetime, such as fluorescent lamps, nitroaniline derivatives of Formula (I) can work with a source of radiations such as a blue light emitting diode (LED) that is very small (about 2 mm or smaller), low cost (2-4 dollars) and has a very long lifetime (up to 100K hours).

This permits the use of nitroaniline derivatives of Formula (I) in a portable device for in situ application.

The support or container can be, for example, a chamber made of optically transparent material containing an aqueous solution of nitroaniline derivatives of Formula (I) at appropriate concentration (up to mM range) or a two dimensional solid substrate bearing a film of nitroaniline derivatives of Formula (I) either in a monolayer form (obtained by self assembling) or in a thicker form (obtained by spin coating) or even a porous solid soaked with nitroaniline derivatives of Formula (I) in a liquid form.

The solid substrate can be, for example, an inorganic base material such as glass, silicon, or quartz, or a plastic polymeric material.

Figure 9:
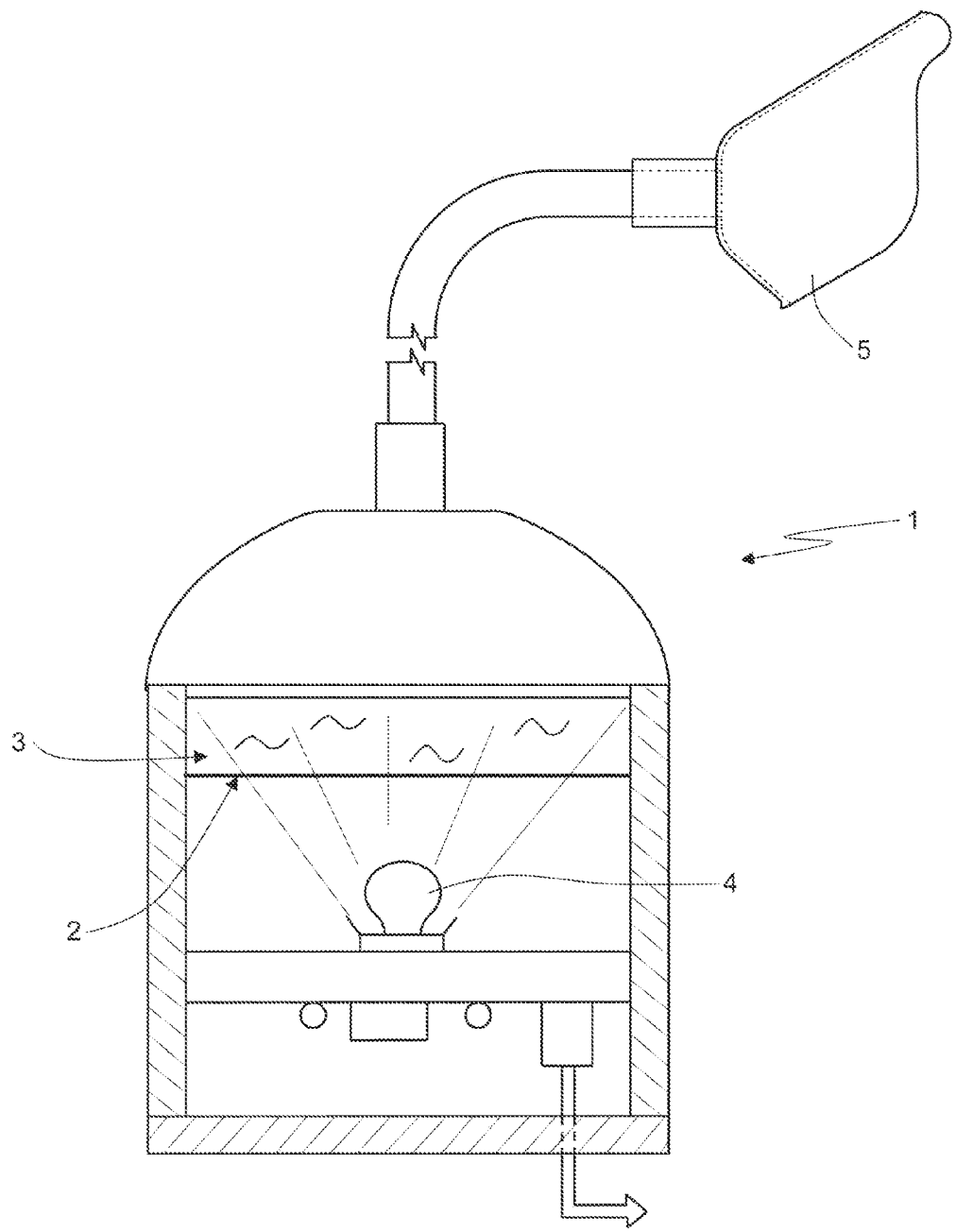
FIG. 9 shows an apparatus for the delivery of the nitroaniline derivatives of Formula (I) in aerosol form.

A scheme of one of the possible systems in which nitroaniline derivatives of Formula (I) can work is shown in FIG. 9.

In detail, FIG. 9 shows an apparatus 1 for the delivery of the nitroaniline derivatives of Formula (I) in aerosol form. The apparatus 1 comprises a container 2 for an aqueous solution 3 of nanoparticles bearing the nitroaniline compound. A source of visible light, e.g., an array 4 of blue LEDs, is arranged below the container 2 and is connected to a power supply (not shown). An inhalator 5 is arranged above the container 2 for administering the nitric oxide generated by the irradiation of the aqueous solution 3 to a patient.

Further characteristics of the present disclosure will appear in the following description of merely illustrative and not limiting examples.

EXAMPLE 1

NO Photo-Release of 4-Nitro-3-(trifluoromethyl)aniline 4-nitro-3-(trifluoromethyl)aniline was dissolved in methanol and the solution was irradiated in a quartz cuvette with 8 lamps emitting radiations with wavelength of 350 nm for 2 hours. The absorbance of the solution was measured every 30 minutes.

It was observed a progressive reduction of the absorbance peak in the band having the lowest energy associated to an increase of the absorbance peak in the band having the highest energy (FIG. 3)

In order to demonstrate the NO release in solution, the Damiani method (P. Damiani, G. Burini, *Talanta* 1986, vol. 33, page 649) conveniently modified by Misko (T. Misko, R. J. Schilling, D. Salvemini, W. Moore, M. Currie, *Anal. Biochem.* 1993, vol. 214, page 11) was used. It allows the indirect determination of NO by measuring nitrite levels. In particular, NO is an highly reactive gas that, in the presence of water, forms an equimolar mixture of nitrites and nitrates. Nitrites, reacting with a DAN (2,3-diaminonaphtalene) solution in the presence of an acid, form 1-naphthotriazole, a highly fluorescent compound having a characteristic UV absorbance.

Therefore, the solution of 4-nitro-3-(trifluoromethyl) aniline in methanol after irradiation was dried and then the recovered 4-nitro-3-(trifluoromethyl)aniline was re-dissolved with water and phosphate buffer 0.1M (pH 7.4). 150 μl of a DAN solution were added to the solution of 4-nitro-3-(trifluoromethyl)aniline heating at 50° C. for 40 minutes. Subsequently, 150 μl of concentrated NaOH was added in order to obtain naphthotriazole ions according to the scheme below.

$$2NO^{\bullet} + O_2 \longrightarrow 2NO_2$$

$$2NO_2^- + H_2O \longrightarrow NO_3^- + NO_2^- + 2H^+$$

2,3-diaminonaphthalene 1H-naphtho[2,3-d][1,2,3]triazole 1H-naphtho[2,3-d][1,2,3]triazole 1H-naphtho[2,3-d][1,2,3]triazole ion The fluorescent spectrum of the solution thus obtained revealed the presence of nitrites and therefore the formation of NO after irradiation of 4-nitro-3-(trifluoromethyl)aniline (FIG. 4).

As shown in FIG. 4, emission peaks of 1-naphtotriazole were clearly identified.

EXAMPLE 2

NO Photo-Releasing of 10-(3-(trifluoromethyl)-4-Nitrophenylamino)decan-1-thiol 10-(3-(trifluoromethyl)-4-Nitrophenylamino)decan-1-thiol was dissolved in a $CH_3OH$:$H_2O$ (10%) solution. This solution was irradiated in a quartz cuvette with 8 lamps emitting radiations with wavelength of 350 nm for 35 minutes. The absorbance of the solution was measured every 30 minutes (FIG. 5).

300 μl of a DAN saturated solution in HCl 0.6 M were added to 3 ml of the irradiated solution of 10-(3-(trifluoromethyl)-4-Nitrophenylamino)decan-1-thiol followed by heating at 50° C. for 20 minutes.

Subsequently, 1 ml of NaOH was added to 1 ml of the solution in order to obtain naphthotriazole ions. The fluorescent spectrum of the solution thus obtained revealed the presence of nitrites and therefore the formation of NO after irradiation of 10-(3-(trifluoromethyl)-4-Nitrophenylamino) decan-1-thiol (FIG. 6). As shown in FIG. 6, emission peaks of 1-naphtotriazole were clearly identified.

EXAMPLE 3

Preparation of Pt-Nanoparticles Functionalized with 10-(3-(Trifluoromethyl)-4-Nitrophenylamino)decan-1-thiol Pt-nanoparticles were prepared according to the scheme below.

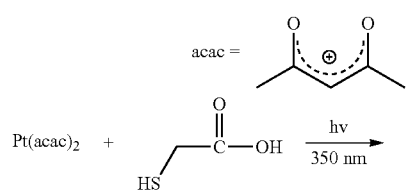

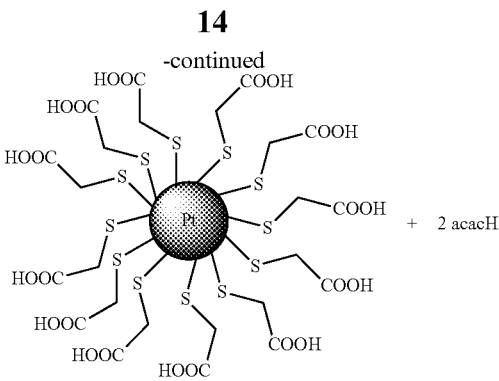

These nanoparticles are soluble in water. TEM analysis revealed the presence of particles having a diameter of about 1 nm.

The functionalization of Pt-nanoparticles as described above with 10-(3-(trifluoromethyl)-4-Nitrophenylamino)decan-1-thiol may be carried out according to the scheme below.

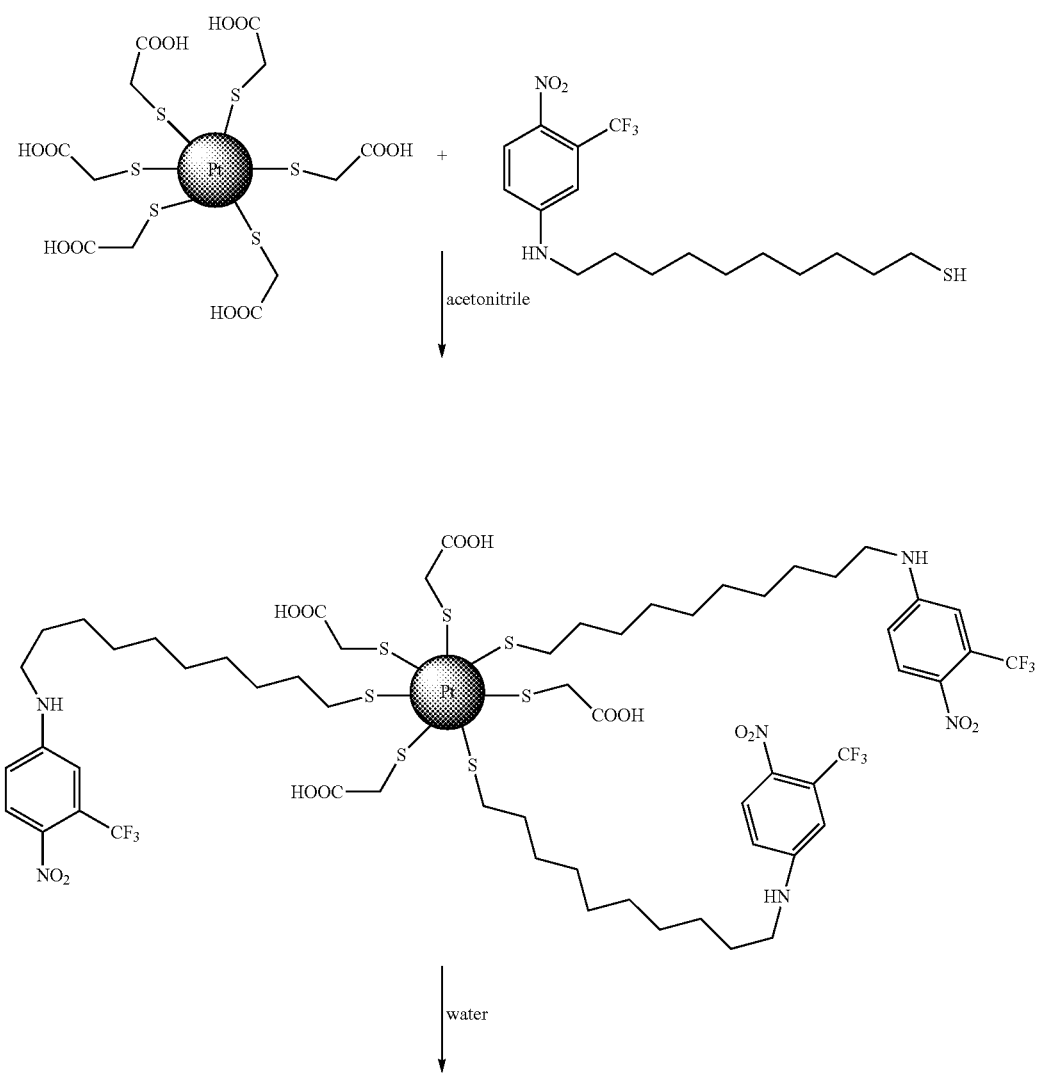

-continued

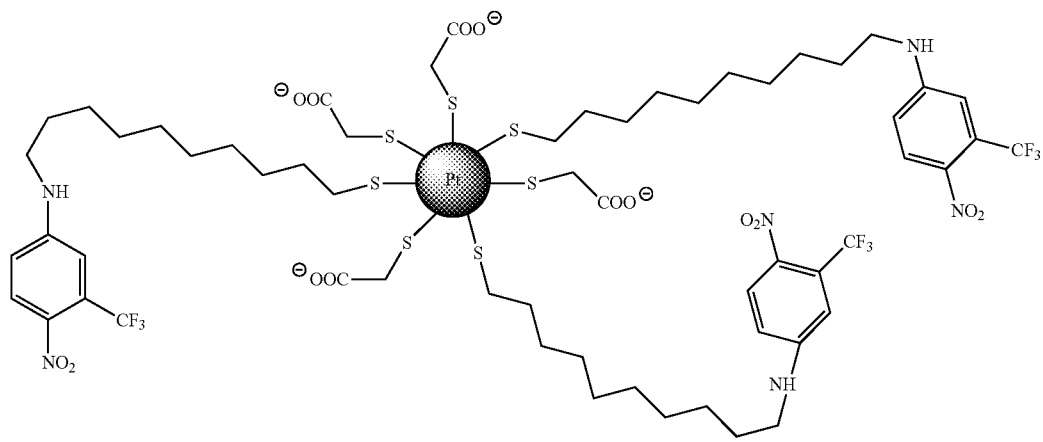

Figure 7:
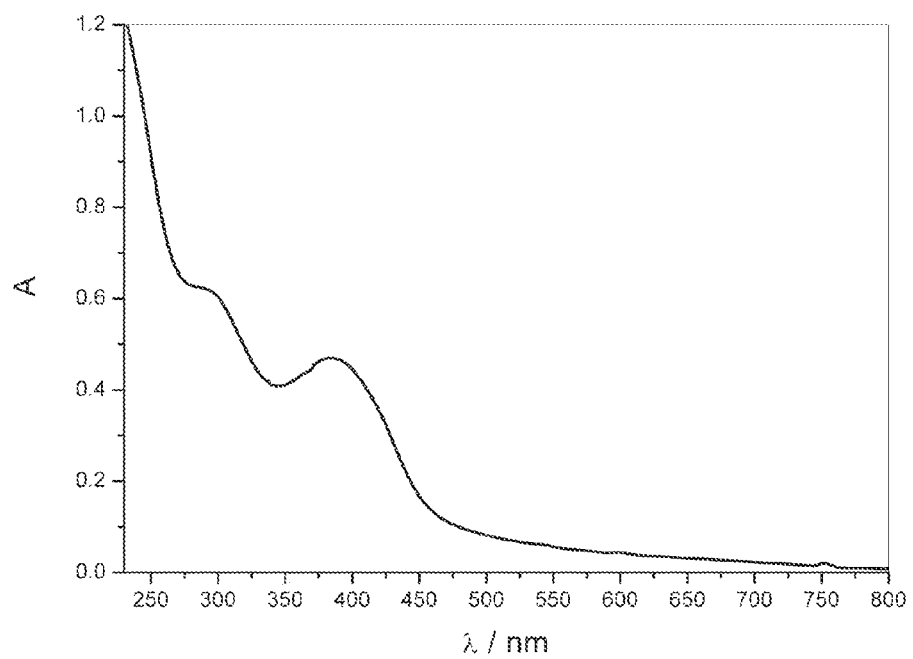
FIG. 7 shows the absorption spectrum of photoactive Pt-nanoparticles.

FIG. 7 reports the absorption spectrum of the photoactive Pt-nanoparticles.

The spectrum clearly shows the typical plasmon absorption band of Pt along with the typical absorption of the photoactive unit at about 420 nm. This proves that the above schemed synthesis was effective.

Figure 8:
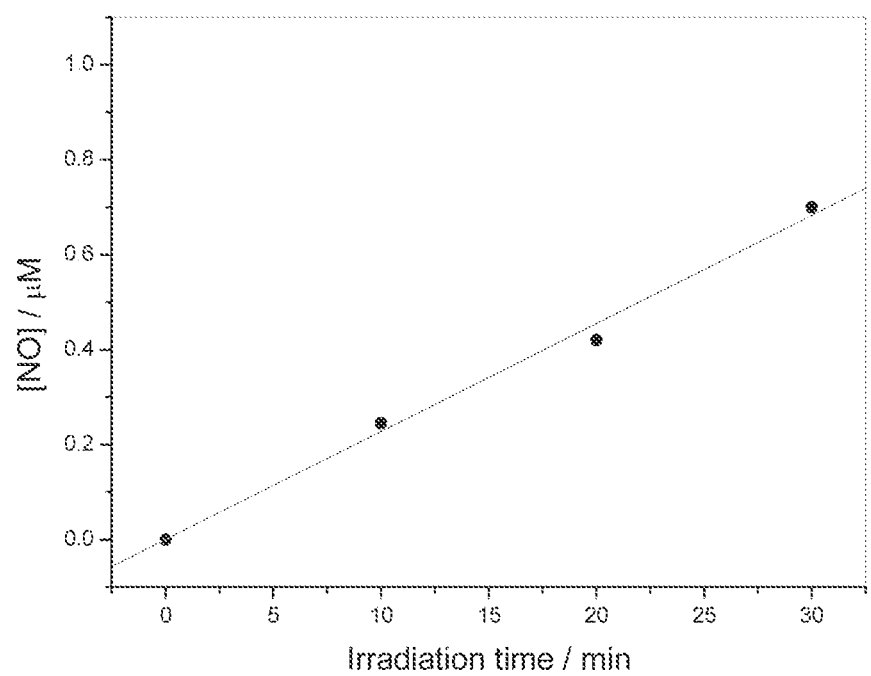
FIG. 8 shows the NO photo-release profile of nanoparticles functionalized with 1043-(trifluoromethyl)-4-Nitrophenylamino)decan-1-thiol.

The NO photo-release of the nanoparticles functionalized with 1043-(trifluoromethyl)-4-Nitrophenylamino)decan-1-thiol was measured using fluorimetric assay based on 2,3-diaminonaphthalene (DAN) [T. P. Misko, R. J. Schilling, D. Salvemini, W. M. Moore, M. G. Currie, *Anal. Chem.*, 1993, vol. 11, pages 214], as shown in Examples 1 and 2 (FIG. 8).

The curve shows the same trend (linear behavior) of the aqueous solution of 10-(3-(trifluoromethyl)-4-Nitrophenylamino)decan-1-thiol.

The Pt-nanoparticles can be used as a delivery agent or carrier for in vivo applications.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A kit comprising:
(1) a nitroaniline derivative of Formula (I):

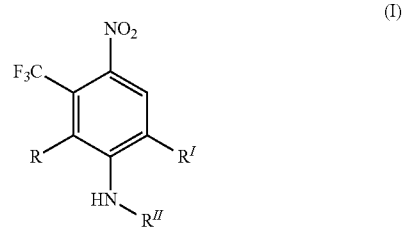

wherein
R and $R^I$ are each independently hydrogen or a $C_1$-$C_3$ alkyl group;
$R^{II}$ is AK-Y, wherein AK is a branched or unbranched $C_2$-$C_{18}$ alkyl group optionally substituted with —OH or NH$_2$ and Y is a tail-group selected from the group consisting of hydrogen, halogen, —SH, —S—SR$^{III}$, Si(OR$^{IV}$)$_3$, —Si—X$_3$ and —CH═CR$^V$R$^{VI}$;
$R^{III}$ is selected from the group consisting of alkyl group, aryl group, aralkyl group, Alkenyl group, alkynyl group and heterocyclic group;
$R^{IV}$ is an alkyl group;
$R^V$ and $R^{VI}$ are independently hydrogen or alkyl group; and
X is halogen; and
(2) a carrier.

2. The kit according to claim 1, wherein said carrier has less than 15% of molar absorptivity of the nitraniline derivative of formula (I) in the wavelength comprised between 300 and 500 nm.

3. The kit according to claim 1, wherein said carrier is a liquid solution.

4. The kit according to claim 1, wherein said carrier is a solid substrate selected from the group consisting of a metal; an inorganic oxide; silicon and a plastic polymeric material.

5. The kit according to claim 4, wherein said nitraniline derivative of Formula (I) is capable of chemically binding to said solid substrate without forming an amide bond.

6. The kit according to claim 5, wherein when said tail-group is —SH or —S—SR$^{III}$, said solid substrate is a metal.

7. The kit according to claim 5, wherein when said tail-group is —Si(OR$^{III}$$_3$)$_3$, or —Si—X$_3$, said solid substrate is an inorganic oxide.

8. The kit according to claim 5, wherein when said tail-group is —CH═CR$^V$R$^{VI}$, said solid substrate is silicon.

9. A system comprising:
a source of radiation having a wavelength of between 300 and 500 nm;
a container containing (1) a nitroaniline derivative of Formula (I):

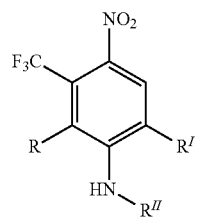

wherein R and R$^I$ are each independently hydrogen or a C$_1$-C$_3$ alkyl group; R$^{II}$ is hydrogen or a substituted or unsubstituted alkyl group; and
(2) a liquid carrier.

10. The system according to claim 9, wherein:
R$^{II}$ is Ak-Y, wherein Ak is a branched or unbranched C$_2$-C$_{18}$ alkyl group optionally substituted with —OH or NH$_2$, and Y is a tail-group selected from the group consisting of hydrogen, halogen, —SH, —S—SR$^{III}$, —Si(OR$^{IV}$$_3$)$_3$, —Si—X$_3$, and —CH═CR$^V$R$^{VI}$;
R$^{III}$ is selected from the group consisting of alkyl group, aryl group, aralkyl group, alkenyl group, alkynyl group and heterocyclic group;
R$^{IV}$ is an alkyl group;
R$^V$ and R$^{VI}$ are independently hydrogen or alkyl group; and X is halogen.

11. The system according to claim 9, wherein said nitroaniline derivative of Formula (I) is 4-nitro-3-(trifluoromethyl) aniline.

12. The system according to claim 9, wherein the source of radiation comprising one or more light emitting diodes.

13. A system comprising:
a source of radiation having a wavelength of between 300 and 500 nm;
a solid substrate coated or soaked with a nitroaniline derivative of Formula (I):

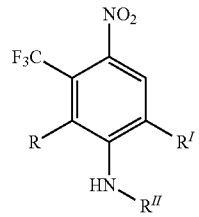

wherein R and R$^I$ are each independently hydrogen or a C$_1$-C$_3$ alkyl group; R$^{II}$ is hydrogen or a substituted or unsubstituted alkyl group;

14. The system according to claim 13 wherein R$^{II}$ is Ak-Y, wherein Ak is a branched or unbranched C$_2$-C$_{18}$ alkyl group optionally substituted with —OH or NH$_2$, and Y is a tail-group selected from the group consisting of hydrogen, halogen, —SH, —S—SR$^{III}$, —Si(OR$^{IV}$$_3$)$_3$, —Si—X$_3$, and —CH═CR$^V$R$^{VI}$;
R$^{III}$ is selected from the group consisting of alkyl group, aryl group, aralkyl group, alkenyl group, alkynyl group and heterocyclic group;
R$^{IV}$ is an alkyl group;
R$^V$ and R$^{VI}$ are independently hydrogen or alkyl group; and X is halogen.

15. The system according to claim 14, wherein said nitroaniline derivative of Formula (I) is 4-nitro-3-(trifluoromethyl) aniline.

16. The system according to claim 13, wherein the source of radiation comprising one or more light emitting diodes.

17. The system according to claim 13 wherein the solid substrate is a metal, a semiconductive material or an inorganic oxide.

18. A kit comprising:
(1) a nitroaniline derivative of Formula (I):

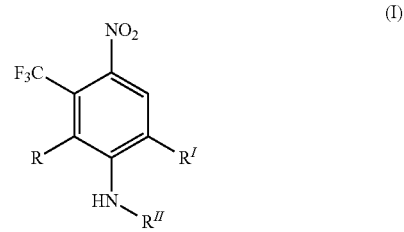

wherein,
R and R$^I$ are each independently hydrogen or a C$_1$-C$_3$ alkyl group; and
R$^{II}$ is hydrogen or a substituted or unsubstituted alkyl group; and
(2) a carrier, wherein said carrier has less than 15% of molar absorptivity of the nitroaniline derivative of Formula (I) in the wavelength comprised between 300 and 500 nm.

19. The kit of claim 18 wherein,
R$^{II}$ is Ak-Y, wherein Ak is a branched or unbranched C$_2$-C$_{18}$ alkyl group optionally substituted with —OH or NH$_2$, and Y is a tail-group selected from the group consisting of hydrogen, halogen, —SH, —S—SR$^{III}$, —Si(OR$^{IV}$$_3$)$_3$, —Si—X$_3$, and —CH═CR$^V$R$^{VI}$;
R$^{III}$ is selected from the group consisting of alkyl group, aryl group, aralkyl group, alkenyl group, alkynyl group and heterocyclic group;
R$^{VI}$ is an alkyl group;
R$^V$ and R$^{VI}$ are independently hydrogen or alkyl group; and X is halogen.

20. A kit comprising:
(1) a nitroaniline derivative of Formula (I):

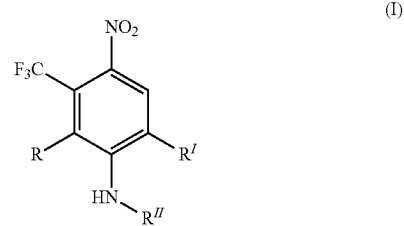

wherein,

R and $R^I$ are each independently hydrogen or a $C_1$-$C_3$ alkyl group;

$R^{II}$ is hydrogen or a substituted or unsubstituted alkyl group; and (2) a carrier, wherein said carrier is a solid substrate selected from the group consisting of a metal; an inorganic oxide; and a plastic polymeric material, wherein said nitroaniline derivative of Formula (I) is capable of chemically binding to said solid substrate without forming an amide bond.

21. The kit of claim 20 wherein solid substrate is gold, platinum and silver, silicon oxide ($SiO_x$) or indium tin oxide (ITO).

* * * * *

UNITED STATES PATENT AND TRADEMARK OFFICE
CERTIFICATE OF CORRECTION

PATENT NO. : 8,766,006 B2
APPLICATION NO. : 13/858558
DATED : July 1, 2014
INVENTOR(S) : Sabrina Conoci et al.

It is certified that error appears in the above-identified patent and that said Letters Patent is hereby corrected as shown below:

In the Claims

Column 16, line 42, claim 1:
"$R^{II}$ is AK-Y, wherein AK is a branched or unbranched" should read, --$R^{II}$ is an Ak-Y, wherein Ak is a branched or unbranched--.

Column 16, line 44, claim 1:
"$NH_2$ and Y is a tail-group selected from the group" should read, --$NH_2$ and Y is a tail-group selected from the group--.

Column 16, line 46, claim 1:
"$Si(OR^{IV}_3)_3$,-$Si$-$X_3$, and -CH=$CR^V R^{VI}$;" should read, --$Si(OR^{IV})_3$, -$Si$-$X_3$, and -CH=$CR^V R^{VI}$;--.

Column 16, line 48, claim 1:
"aryl group ,aralkyl group, Alkenyl group, alkynyl group" should read, --aryl group, aralkyl group, alkenyl group, alkynyl group--.

Column 16, line 55, claim 1:
"than 15% of molar absorptivity of the nitraniline derivative of" should read, --than 15% of molar absorptivity of the nitroaniline derivative of--.

Column 16, line 56, claim 1:
"formula (I) in the wavelength comprised between 300 and" should read, --Formula (I) in the wavelength comprised between 300 and--.

Column 17, line 64, claim 13:
"alkyl group;" should read, --alkyl group.--.

Signed and Sealed this
Thirty-first Day of March, 2015

Michelle K. Lee
*Director of the United States Patent and Trademark Office*

CERTIFICATE OF CORRECTION (continued)
U.S. Pat. No. 8,766,006 B2

Column 18, line 2, claim 14:
"halogen, -SH, -S-SR$^{III, Si(OR^{IV}}$$_3)_3$, -Si-X$_3$, and" should read, --halogen, -SH, -S-SR$^{III}$, -Si(OR$^{IV}$$_3)_3$, -Si-X$_3$, and--.

Column 18, line 50, claim 19:
"R$^{VI}$ is an alkyl group;" should read, --R$^{IV}$ is an alkyl group;--.